US008632796B2

(12) United States Patent
Cooper

(10) Patent No.: US 8,632,796 B2
(45) Date of Patent: Jan. 21, 2014

(54) CALCIUM PHOSPHATE/SULFATE-BASED BONE IMPLANT COMPOSITION

(75) Inventor: John Joseph Cooper, Crewe (GB)

(73) Assignee: Biocomposites Limited (GB)

( * ) Notice: Subject to any disclaimer, the term of this patent is extended or adjusted under 35 U.S.C. 154(b) by 413 days.

(21) Appl. No.: 12/356,357

(22) Filed: Jan. 20, 2009

(65) Prior Publication Data

US 2009/0124536 A1    May 14, 2009

Related U.S. Application Data

(62) Division of application No. 10/476,242, filed as application No. PCT/GB02/01986 on May 1, 2002, now abandoned.

(30) Foreign Application Priority Data

May 2, 2001    (GB) .................................. 0110726.7

(51) Int. Cl.
| | | |
|---|---|---|
| *A61F 2/00* | (2006.01) | |
| *A61K 9/14* | (2006.01) | |
| *A01N 59/26* | (2006.01) | |
| *A61K 33/42* | (2006.01) | |
| *A01N 59/06* | (2006.01) | |
| *A61K 33/06* | (2006.01) | |

(52) U.S. Cl.
USPC ............ 424/423; 424/489; 424/602; 424/696

(58) Field of Classification Search
None
See application file for complete search history.

(56) References Cited

U.S. PATENT DOCUMENTS

| | | | |
|---|---|---|---|
| 4,778,471 A | 10/1988 | Bajpai | |
| 5,149,368 A * | 9/1992 | Liu et al. ....................... | 424/602 |
| 5,679,723 A * | 10/1997 | Cooper et al. ................ | 523/115 |
| 5,824,087 A | 10/1998 | Aspden et al. | |
| 6,224,635 B1 * | 5/2001 | Ricci et al. ................. | 623/23.62 |
| 2001/0032022 A1 | 10/2001 | Ricci et al. | |

FOREIGN PATENT DOCUMENTS

| | | |
|---|---|---|
| EP | 94400608.9 | 9/1994 |
| JP | 3261643 A | 11/1991 |
| JP | 7002691 A | 1/1995 |
| JP | 7008548 A | 1/1995 |
| JP | 2000 159564 A | 6/2000 |

OTHER PUBLICATIONS

Ohura K et al., Resorption of, and bone formation from, new beta-tricalcium phosphate-monocalcium phosphate cements: an in vivo study, Journal of Biomedical Materials Research. Feb. 1996, 193-200, vol. 30-No. 2, United States.
Pepelassi E M et al., "Doxycycline-tricalcium phosphate composite graft facilitates osseous healing in advanced periodontal furcation defects," Journal of Periodontology. Feb. 1991, 106-115, vol. 62-No. 2, United States.
Kenaga M et al.Blomechanical characterization of a biodegradable calcium phosphate hydraulic cement: a comparison with porous biphasic Calcium phosphate ceramics, Journal of Biomedical Materials Research. Apr. 1998, 139-144, vol. 40-No. 1, United States.
Ohura K et al., "Healing of segmental bone defects in rats induced by a beta-TCP-MCPM cement combined with rhBMP-2," Journal of Biomedical Materials Research. Feb. 1999, vol. 44-No. 2, United States.
"Zinc" Oxide; Toxic Chemical Release Report; Community Right-to-Know, Federal Register Environmental Documents, Sep. 12, 1995, p. 3, Accessed online on Dec. 7, 2007 at http://www.epa.gov/fedrgster/EPA-TRI/1995/September/Day-12/pr-25.htrnl.
International Search Report International Application; U.S. Appl. No. PCT/GB02/01986; 6 pgs, Oct. 15, 2002.

* cited by examiner

Primary Examiner — Carlos Azpuru
Assistant Examiner — Casey Hagopian
(74) Attorney, Agent, or Firm — Tarolli, Sundheim, Covell & Tummino LLP

(57) ABSTRACT

A bone implant composition, the composition comprising calcium sulphate and slowly soluble source of calcium, orthophosphate and hydroxyl ions. The composition may be provided in powder or granulated form.

15 Claims, No Drawings

CALCIUM PHOSPHATE/SULFATE-BASED BONE IMPLANT COMPOSITION

CROSS REFERENCES TO RELATED APPLICATIONS

The following application is a divisional application that claims priority to: U.S. application Ser. No. 10/476,242, filed Mar. 25, 2004, that claims priority to International Application Serial No. PCT/GB02/01986, filed May 1, 2002; which claims priority to Great Britain. Application Serial No. 0110726.7, filed May 2, 2001. The following divisional application claims priority to the aforementioned applications for all purposes and incorporates the aforementioned applications by reference in their entireties for all purposes.

FIELD OF THE INVENTION

This invention concerns a bone implant composition, and a method of forming a bone graft.

BACKGROUND

In orthopedic and dental surgical applications there is a great need for biocompatible and bioresorbable implant material which can be conveniently and effectively used as a bone substitute. This includes bone lost due to periodontal disease, ridge augmentation, sinus elevation, bone defects or cavities due to trauma, disease or surgery and spinal fusions. Following implantation the bone substitute is ideally resorbed in a time frame which is consistent with its replacement by new vital bone.

The bone graft material of preferred choice is autograft, i.e. the patients own bone, since this is totally biocompatible, is not subject to an immune response or disease transmission and has good osteogenic capacity. However, its source is limited, it requires a second surgical procedure for harvest and there are often donor site morbidity problems.

Allograft bone is usually considered an acceptable alternative since it is more readily available and has a reasonable level of efficacy. However, it has the potential for disease transmission and since it is 'foreign' tissue there is the potential for immunological reactions. In addition, it is a material variable in its properties, due to donor source (often elderly people with osteoporotic bones) and processing variability. This makes prediction of clinical outcome difficult when allograft is used. Delayed healing is a frequent complication.

DISCLOSURE OF THE INVENTION

According to the present invention there is provided a bone implant composition, the composition comprising calcium sulphate and slowly soluble sources of calcium, orthophosphate and hydroxyl ions.

The source of the ions is preferably provided by compounds which are slowly soluble in water, and preferably compounds where the water solubility at room temperature is less than 5 g per liter, desirably less than 1 g per liter, and more desirably less than 0.1 g per liter.

The source of the calcium ions may be the calcium sulphate alone, or may be provided by one or more of: calcium carbonate, calcium phosphate, calcium oxide, calcium fluoride, calcium citrate, calcium stearate, or dolomite.

The calcium sulphate may be in the form of dihydrate, hemi-hydrate, soluble anhydrite or insoluble anhydrite. The ratio of calcium sulphate to all other compounds in the composition is preferably between 0.2 and 2 parts by weight.

The composition may also comprise a medicament, and desirably in an effective therapeutic amount. The medicament may comprise any of: an antibiotic, an anti-cancer agent, or bone morphogenic protein.

The source of orthophosphate ions may be one or more of: hydroxyapatite, alpha tricalcium phosphate, beta tricalcium phosphate, dicalcium phosphate, tetracalcium phosphate or magnesium orthophosphate. The source of orthophosphate ions may be in the form of a micro-porous granular solid. The granules may have a particle size in the range 0.2-5.00 mm. The source of orthophosphate may be in the form of a microporous granular solid component.

The source of the hydroxyl ions may be one or more of: calcium oxide, insoluble anhydrite, calcium hydroxide, magnesium oxide, magnesium hydroxide, zinc oxide, zinc hydroxide, or basic magnesium carbonate.

In the composition the ratio of basicity to orthophosphate is preferably between 0.0 and 1.0 molar.

The composition may be in the form of a powder which can be mixed with water or an aqueous solution to form a usable paste.

Alternatively, the composition may be in the form of granules or pellets. The composition may be formed into pellets using a tablet press.

The invention also provides a method of forming a bone graft, the method comprising using a bone implant composition according to any of the preceding ten paragraphs.

When in powder form the composition may be mixed with water or an aqueous solution to form a putty or paste prior to application. The putty or paste may be applied to a surgical site by a suitable applicator such as a syringe. Alternatively the putty or paste may be applied to a mould and allowed to set prior to presentation to the surgical site.

Where the composition is in the form of granules or pellets, the granules or pellets can be packed into a bone cavity.

Embodiments of the present invention will now be described by way of example only.

EXAMPLE 1

A powdered mixture was prepared according to the following composition:—

1.25 g beta tricalcium phosphate
0.63 g calcium sulphate alpha hemihydrate
0.05 g magnesium oxide The beta tricalcium phosphate particles have a size of 250-500 microns.

The mixture was blended with 0.85 ml of a 1% potassium sulphate solution to give a paste which was used to fill a periodontal pocket.

EXAMPLE 2

A powdered mixture was prepared according to the following composition:—

35.0 g beta tricalcium phosphate granules with a particle size of 1-2 mm diameter.
17.5 g calcium sulphate dihydrate
2.2 g magnesium oxide
0.80 g calcium stearate The mixture was pressed into pellets 3 mm diameter by 2.5 mm deep using a tablet press. The pellets were used to fill a bone cavity.

EXAMPLE 3

A powdered mixture was prepared according to the following composition:—
- 35.0 g alpha tricalcium phosphate
- 14.0 g anhydrous calcium sulphate-insoluble form
- 10.0 g basic magnesium carbonate
- 0.1 g zinc oxide The mixture was pressed into pellets using a tablet press.

EXAMPLE 4

A powdered mixture was prepared according to the following composition:—
- 10.0 g beta tricalcium phosphate particles
- 5.0 g calcium sulphate alpha hemihydrate powder
- 0.5 g magnesium oxide The beta tricalcium phosphate particles have a size range of 1-2 mm.

The mixture was blended with 9.5 ml of water and compacted into 6 mm diameter cylindrical moulds where it was allowed to set. The set pellets were removed from the moulds and allowed to dry. These were used to fill a bone cavity.

EXAMPLE 5

A powdered mixture was prepared according to the previous example (Example 4), but including 5% by weight of the antibiotic gentamycin which was added to the powdered mix prior to moulding.

There is thus described a bone implant composition and a method of using same which provides for considerable advantages. The composition is based upon the following chemical equation:—

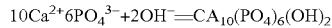

$$10Ca^{2+} 6PO_4^{3-} + 2OH^- = CA_{10}(PO_4)_6(OH)_2$$

The composition provides a source of ions which precipitate in vivo to provide a poorly crystalline, substituted apatite which closely mimics the natural mineral phase of bone, in contrast to other presently available synthetic bone graft substitutes. Also, the reaction occurs over a time frame commensurate with the body's ability to regenerate new healthy bone. This precipitated hydroxyapatite is amenable to osteoclastic resorption. The calcium sulphate phase initially present resorbs by a simple dissolution mechanism over a period of a few weeks to provide a macroporous structure amenable to vascularisation and invasion by new bony tissue. The calcium sulphate forms a micro-porous barrier which prevents intrusion of unwanted soft tissue (cells) in the immediate post implantation period.

The source of ortho phosphate is preferably a micro-porous granular solid, with a particle size of 0.2-5 mm. This size range provides for an intergranule pore size of 100-200 microns which is necessary for cell infiltration and vascularization to stimulate new bone in-growth.

Various modifications may be made without departing from the scope of the invention. The calcium ions may be obtained from the calcium sulphate alone, or may also be obtained from calcium stearate as in Example 2, or other calcium compounds such as calcium carbonate, calcium phosphate, calcium oxide, calcium fluoride, calcium citrate or dolomite. In addition or as an alternative to the orthophosphate ions being provided by beta tricalcium phosphate, these ions may be provided by hydroxyapatite, alpha tricalcium phosphate, dicalcium phosphate, tetracalcium phosphate or magnesium orthophosphate.

In the examples the source of hydroxyl ions is magnesium oxide, and also zinc oxide in Example 3. These ions may though additionally or as an alternative be obtained from calcium oxide, insoluble anhydrite, calcium hydroxide, magnesium hydroxide, zinc hydroxide or basic magnesium carbonate. As illustrated in the Examples, the calcium sulphate may be in one or more of the following forms:—alpha hemihydrate, beta hemihydrate, soluble anhydrite, insoluble anhydrite or dihydrate.

The composition may comprise a medicament in an effective therapeutic amount, which medicament may comprise an antibiotic, an anti-cancer agent, or bone morphogenic protein.

Whilst endeavouring in the foregoing specification to draw attention to those features of the invention believed to be of particular importance it should be understood that the Applicant claims protection in respect of any patentable feature or combination of features hereinbefore referred to whether or not particular emphasis has been placed thereon.

The invention claimed is:

1. A ceramic bone graft composition consisting of beta-tricalcium phosphate, calcium sulphate and slowly soluble sources of calcium ions and hydroxyl ions, where the calcium ions are provided by calcium sulphate alone or by one or more selected from the group consisting of calcium phosphate, calcium oxide, calcium citrate, calcium searate, or calcium dolomite, the hydroxyl ions being provided by one or more selected from the group consisting of calcium oxide, insoluble anhydrite, calcium hydroxide, zinc oxide, zinc hydroxide and basic magnesium carbonate, wherein the beta-tricalcium phosphate is in the form of granules having a particle size in the range 0.5-2.0 mm.

2. A ceramic bone graft composition according to claim 1 wherein water solubility of the ceramic bone graft composition at room temperature is less than 1 gram per liter.

3. A ceramic bone graft composition according to claim 1 wherein water solubility of the ceramic bone graft composition at room temperature is less than 0.1 gram per liter.

4. A ceramic bone graft composition according to claim 1, characterised in that the calcium sulphate is selected from the group consisting of dihydrate, hemi-hydrate, soluble anhydrite and insoluble anhydrite.

5. A ceramic bone graft composition according to claim 1 where the composition is in the form of granules or powder.

6. A ceramic bone graft material according to claim 1, wherein the bone graft material can be formed into pellets using a tablet press.

7. A ceramic bone graft material according to claim 6 where the pellets are allowed to set prior to being used to fill a bone cavity.

8. A method of treating a bone defect by applying the ceramic bone graft material according to claim 7 and packing it into a bone cavity.

9. A method of applying a ceramic bone graft composition according to claim 1 to a surgical site using a suitable applicator.

10. A method according to claim 9, wherein the suitable applicator is a syringe.

11. A ceramic bone cement according to claim 6, wherein the pellets are 3 mm in diameter by 2.5 mm deep.

12. A ceramic bone graft composition consisting of beta-tricalcium phosphate, calcium sulphate and slowly soluble sources of calcium ions and hydroxyl ions, where the calcium ions are provided by calcium sulphate alone or by one or more selected from the group consisting of calcium phosphate, calcium oxide, calcium citrate, calcium stearate, or dolomite, the hydroxyl ions being provided by one or more selected from the group consisting of calcium oxide, insoluble anhydrite, calcium hydroxide, zinc oxide, zinc hydroxide and basic magnesium carbonate, and wherein the beta-tricalcium phosphate is in the form of granules having a particle size in the range 0.5-2.0 mm, and wherein the ceramic bone graft composition is able to be formed into a usable paste or putty.

13. A ceramic bone graft composition according to claim 12 wherein the composition can be formed into a usable paste or putty by the addition of water or an aqueous liquid.

14. A ceramic bone graft composition according to claim 12 characterised in that the paste or putty can be applied to a mould to be formed into pellets.

15. A ceramic bone graft composition according to claim 12 wherein the paste provides a macroporous structure in-situ.

* * * * *